United States Patent [19]

Bomback

[11] 4,372,748

[45] Feb. 8, 1983

[54] METHOD OF DETERMINING VEHICLE MISFUELING

[75] Inventor: John L. Bomback, Plymouth, Mich.

[73] Assignee: Ford Motor Company, Dearborn, Mich.

[21] Appl. No.: 293,548

[22] Filed: Aug. 17, 1981

[51] Int. Cl.$^3$ .................... G01N 31/06; G01N 23/00
[52] U.S. Cl. ........................ 436/73; 422/88; 422/91; 422/92
[58] Field of Search ............ 23/232 R, 232 E; 422/58, 86, 88, 91, 92; 378/45-49

[56] References Cited

U.S. PATENT DOCUMENTS

| | | | |
|---|---|---|---|
| 2,787,903 | 4/1957 | Beard | 73/23 |
| 3,174,325 | 3/1965 | Redhead | 73/23 |
| 3,332,745 | 7/1967 | Bailey et al. | 23/232 R |
| 3,431,771 | 3/1969 | Tsien | 73/23 |
| 3,941,566 | 3/1976 | Roche | 23/230 R |
| 4,143,316 | 3/1979 | Roy et al. | 73/19 |
| 4,192,175 | 3/1980 | Godai et al. | 73/19 |

OTHER PUBLICATIONS

Hirschler et al., I & E.C., vol. 49(7) 1957, pp. 1131-1142.
Leichnitz, Detector Tube Handbook, 4th Ed. 1979, pp. 196-197.

Primary Examiner—Michael S. Marcus
Attorney, Agent, or Firm—William E. Johnson; Olin B. Johnson

[57] ABSTRACT

A method of determining if an internal combustion engine has been operated on a leaded fuel. The method has the following general steps. A misfueling detector is formed from a material which is capable of interacting with lead when exhaust gases containing lead are passed thereover. The interacting lead alters at least one measurable characteristic of the misfueling detector. The misfueling detector is placed in an exhaust system and exhaust gases from an internal combustion engine are allowed to pass thereover. The misfueling detector is removed from the exhaust system and the measurable characteristic thereof is measured to determine whether or not the misfueling detector had absorbed lead therein while located in the exhaust system of the internal combustion engine.

6 Claims, 3 Drawing Figures

METHOD OF DETERMINING VEHICLE MISFUELING

BACKGROUND OF THE INVENTION AND PRIOR ART STATEMENT

In recent years, catalytic converters have been used extensively in treating exhaust gases from internal combustion engines. This is particularly true in the area of internal combustion engines used in automotive vehicles.

When an automotive vehicle is equipped with a catalytic converter, it is necessary for the operator of the vehicle to use unleaded gasoline as the fuel. This requirement is caused by the fact that a leaded gasoline will deteriorate the activity of the catalytic converter. More particularly, the lead used in a leaded fuel acts as a poison for most materials used as catalysts for motor vehicles. Lead will deactivate catalysts formed from materials such as platinum, palladium, ruthenium, rhodium, iridium, etc. Once deactivated, these catalysts are no longer effective in treatment of the exhaust gases.

Some operators of vehicles which are required to be operated on unleaded fuel only will, in fact, use a leaded fuel in the vehicle. Basically, the reason for using a leaded fuel is an economic one since leaded fuels are generally several cents per gallon less than unleaded fuels.

Thus, for those manufacturers who equip internal combustion engines with catalytic exhaust treatment devices, it is important to know whether or not the internal combustion engine has used leaded fuel during its operation. For example, if the operator of a catalytically equipped automobile returns the vehicle under warranty and requests a new catalytic converter to replace a defective one, it is important to determine if the catalytic converter was rendered ineffective because the user burned leaded fuel during operation of the vehicle. If the operator of the vehicle has been misfueling the vehicle, that is, putting leaded fuel in the vehicle when unleaded fuel is required, he then is solely responsible for the damage to the catalytic converter. In such an instance, the operator of the vehicle must stand the cost of replacement of the very expensive catalytic converter, rather than the company who manufactures the same.

It is, therefore, a principal object of this invention to provide a method of determining if an internal combustion engine has been operated by burning a leaded fuel therein, which method is simple and efficient in operation and positive in results.

It is still another object of this invention to provide a method of determining if an internal combustion engine has been operated by burning a leaded fuel, which method gives an integrated overall value for the amount of leaded fuel which has been burned in the engine.

A prior art search was conducted on the subject matter of this specification in the public search room of the U.S. Patent Office. This search resulted in the citation of six patents, none of which resembles the method set forth in this specification. The patents cited and the reasons why they are not germane are set forth below.

U.S. Pat. No. 2,787,903 is directed primarily to separating a corrosive gas from a gas sample to be analyzed. The device disclosed is based on the permeability of gases through a material and it does not measure an integrated exposure.

U.S. Pat. No. 3,174,325 is directed to improvements in instruments for qualitatively analyzing gases. The device disclosed detects gases which are desorbed selectively from the surface of a porous solid as the temperature of that solid is raised.

U.S. Pat. No. 3,431,771 is directed to an instrument used for qualitative and quantitative detection of a gas in a mixture of various gases. The gas under test is admitted to the test device in a mixture of gases and is selectively absorbed by an absorbant after passing through a microporous element of accurately controlled porosity. A device is provided for measuring electrical resistance changes in the absorbant whereby the properties of the absorbable gas may be indicated.

U.S. Pat. No. 3,941,566 is directed to a device for determining carbon activity through a pressure measurement. The device is fairly complex and it is designed to measure instantaneous activity of carbon in molten metal.

U.S. Pat. No. 4,143,316 is directed to a diffusion type hydrogen meter for improving the sensitivity and response time for the measurement of hydrogen in liquid sodium. This device is based on the diffusion of hydrogen through a solid and measures the instantaneous hydrogen concentration in liquid sodium.

U.S. Pat. No. 4,192,175 discloses a process and apparatus for measurement of diffusable hydrogen within a metal. This device may be used to measure hydrogen in steel.

SUMMARY OF THE INVENTION

This invention relates to a method of determining if an internal combustion engine has been operated by burning a leaded fuel therein.

In accordance with the general principles of the method of this invention, a misfueling detector is formed from a material which is capable of interacting with lead when exhaust gases containing lead are passed thereover. The interacting lead alters at least one measurable characteristic of the misfueling detector.

The misfueling detector is placed in an exhaust system associated with the internal combustion engine. Exhaust gases from the internal combustion engine are allowed to flow over the misfueling detector. The misfueling detector is removed from the exhaust system associated with the internal combustion engine. The measurable characteristic of the misfueling detector is measured to determine whether the misfueling detector had absorbed lead therein while located in the exhaust system of the internal combustion engine.

In accordance with an illustrated preferred embodiment of the method of this invention, the misfueling detector is formed from a glass composition which will absorb lead. The amount of lead absorbed in the glass body is measured by floating the body in water to determine the amount of water that that body displaces, the measurement being indicative of the amount of lead absorbed therein. Other ways of detecting lead in the body are, of course, by weighing the same or by taking an x-ray fluorescence spectrum thereof.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of specific embodiments when read in connection with the accompanying drawings, wherein like reference characters indicate like parts throughout the several figures, and in which:

DESCRIPTION OF THE PREFERRED EMBODIMENT

Figure 1:
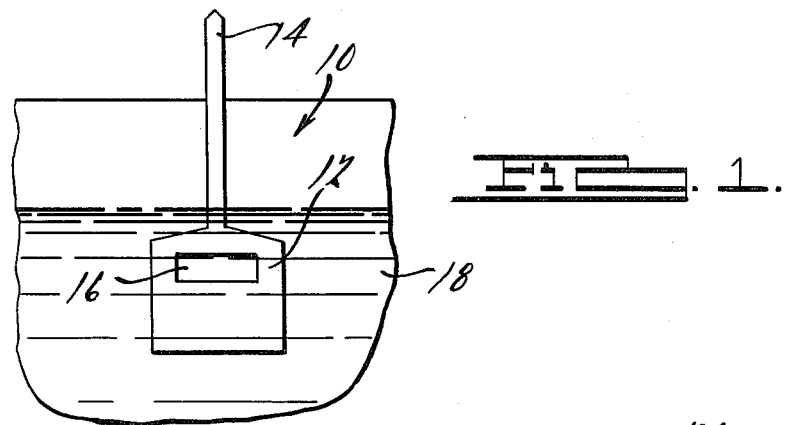
FIG. 1 is a schematic drawing of a misfueling detector having a characteristic thereof measured prior to its use in an exhaust system of an internal combustion engine.

The following description is what I consider to be a preferred embodiment of my method of detecting the misfueling of an internal combustion engine. The following description also sets forth what I now contemplate to be the best mode of carrying out the method of this invention. This description is not intended to be a limitation upon the broader principles of this method, and while preferred materials are used to illustrate the method in accordance with the requirements of the patent laws, it does not mean that the method is operative only with the stated materials, as others may be substituted therefor.

Also, for example, the method disclosed herein may be successfully used with materials yet to be developed by skilled artisans such as new forms of ceramic materials which would interact with lead as, for example, by absorbing the same. It is therefore contemplated by me that the method disclosed in this specification may also be successfully used with materials which are yet to be developed because the the principles of operation of the method remain the same, regardless of the particular material used with the method so long as that material is one which interacts with lead in a manner that the lead alters at least one measurable characteristic of the material.

The method of this invention is initiated by forming a misfueling detector, generally identified by the numeral 10. This detector is formed from a material which is capable of interacting with lead when exhaust gases containing lead are passed thereover. In accordance with the preferred embodiment of this invention, the misfueling detector is formed from a glass such as silica glass. This type of glass interacts with lead by absorbing the same if the exhaust gases passing thereover contain lead. By absorbing lead, I mean lead containing compounds absorb on the glass surface and decompose into lead oxide which is soluble in silica glass. The lead oxide subsequently diffuses into the glass structure due to the high temperature of the exhaust gas.

In accordance with the preferred embodiment of this invention, the misfueling detector 10 has a float portion 12 and a gauge portion 14, the purpose of which will be described below. Also, in accordance with the teachings of a preferred embodiment of the method of this invention, the misfueling detector has an internal void 16 to control the float characteristics of the detector in a fluid such as water 18. The misfueling detector is formed so that when it is initially made, the float portion 12, when floated in water, will generally lie below the surface of the water while a prescribed length (d) of the gauge portion thereof extends out of the water. The measurable characteristic of the preferred embodiment of the misfueling detector is the length (d) from which the gauge portion 14 of the misfueling detector 10 extends above the water 18 at a time before it has been exposed to the exhaust gases from an internal combustion engine.

Figure 2:
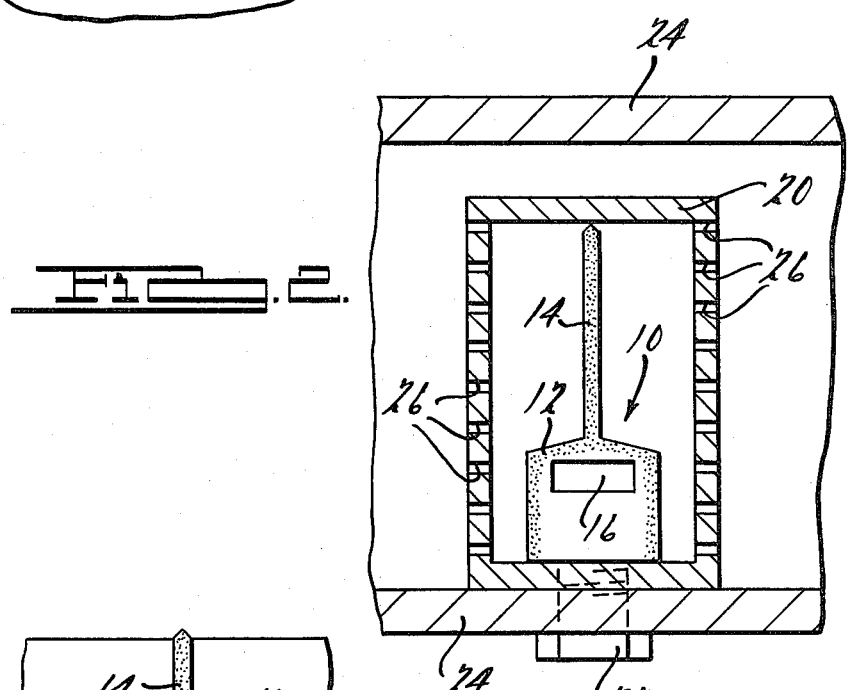
FIG. 2 is a schematic drawing of the misfueling detector installed in the exhaust system of the internal combustion engine.
Figure 3:
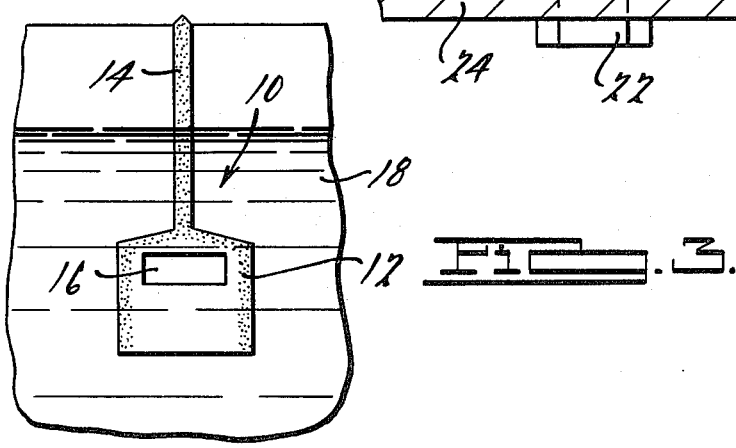
FIG. 3 is a schematic drawing of the misfueling detector having a characteristic thereof measured after it has been exposed to the exhaust gases from the internal combustion engine which pass through the exhaust system.

FIG. 2 is a pictorial presentation of the next step in my method. In this step, the misfueling detector 10 is placed in a confining structure 20 which is suitably secured as, for example, by means of a threaded fastener 22 to an exhaust duct 24 of an exhaust system which carries exhaust gases from an internal combustion engine. The confining structure 20 has a plurality of openings 26 therethrough which allow some of the exhaust gases flowing through the exhaust duct 24 to pass through the confining structure 20. In this manner, the exhaust gases from the internal combustion engine are allowed an opportunity to pass over the misfueling detector 10.

If the exhaust gases passing over the misfueling detector 10 contain lead, the lead will interact with the misfueling detector. In accordance with the teachings of the preferred embodiment, the interaction is one in which the lead is absorbed by the glass material forming the misfueling detector. This absorbtion is principally along the surfaces of the misfueling detector which are exposed to the exhaust gases. However, there is some transport of lead into the body. The amount of absorbtion of lead, of course, depends on the amount of leaded fuel which is burned in the internal combustion engine. If the vehicle is operated at all times on unleaded fuel, then there is an insignificant amount of lead in the exhaust gases and therefore little, if any, lead will be picked up by the device. However, if the operator of the vehicle continuously uses a leaded fuel, very significant quantities of lead will be absorbed into the misfueling detector.

Use of such a misfueling detector comes into play if the operator of the vehicle alleges and it is found that the catalyst system of the vehicle is defective. If the vehicle has been operated on unleaded fuel and is still within the warranty period, it is the responsibility of the automobile manufacturer to replace the rather costly catalyst system. However, if the vehicle has been operated improperly, that is, by burning a leaded fuel, the catalyst system warranty is not in effect and it is the responsibility of the operator to replace the same.

When an argument arises as to the responsibility for replacing the catalyst system, the misfueling detector comes into play in the following manner. The misfueling detector 10 is removed from the confining structure 20 which had mounted the same in the exhaust duct 24. The misfueling detector is then once again refloated in water. If lead had been contained in the exhaust gases, and a portion of that lead has been picked up by the misfueling detector, a significantly shorter amount of the gauge portion 14 of the misfueling detector will remain above the surface of the water when the misfueling detector 10 is once again floated. The decrease in the dimension (d) is an integrated measurement of the total amount of leaded fuel which has been burned in the internal combustion engine. If the amount of lead measured by the misfueling detector is significant, then the responsibility for replacing a defective catalytic converter which has been fouled and deactivated by the lead contaminant is the responsibility of the operator of the vehicle.

A preferred embodiment of the method of this invention has been disclosed. The misfueling detector was floated in water in order to measure a measurable characteristic thereof which changes as that device interacts with lead. Other ways of accomplishing this same type of measurement could be by weighing a misfueling detector, chemically analyzing such a detector, or running x-ray analysis on such a detector. Many other embodiments may also be through up by a skilled artisan.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of this invention.

What is claimed is:

1. A method of determining if an internal combustion engine has been operated by burning a leaded fuel therein which comprises the steps of:
    forming a misfueling detector from a glass material which is capable of absorbing lead when exhaust gases containing lead are passed thereover, said absorbed lead altering at least one measurable characteristic of the misfueling detector;
    placing said misfueling detector in an exhaust system associated with an internal combustion engine;
    allowing exhaust gases from the internal combustion engine to pass over said misfueling detector so that lead in said exhaust gases is absorbed by said detector;
    removing said misfueling detector from the exhaust system associated with the internal combustion engine; and
    measuring said measurable characteristic of said misfueling detector to determine whether or not said misfueling detector had absorbed lead therein while located in the exhaust system of the internal combustion engine.

2. The method of claim 1, in which said measurable characteristic of said misfueling detector is a physical characteristic.

3. The method of claim 2, in which said measurable physical characteristic of said misfueling detector is density.

4. The method of claim 2, in which said measurable physical characteristic of said misfueling detector is weight.

5. The method of claim 1, in which said measurable characteristic of said misfueling detector is a chemical characteristic.

6. The method of claim 5, in wich said measurable chemical characteristic of said misfueling detector is an x-ray fluorescence spectrum.

* * * * *